United States Patent
Akazawa

(10) Patent No.: US 9,839,401 B2
(45) Date of Patent: Dec. 12, 2017

(54) RADIATION TOMOGRAPHY APPARATUS

(71) Applicant: Shimadzu Corporation, Kyoto (JP)

(72) Inventor: Ayako Akazawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 62 days.

(21) Appl. No.: 15/000,099

(22) Filed: Jan. 19, 2016

(65) Prior Publication Data

US 2017/0202522 A1 Jul. 20, 2017

(51) Int. Cl.
G06K 9/00 (2006.01)
A61B 6/03 (2006.01)
G06T 11/60 (2006.01)
G06T 7/00 (2017.01)
A61B 6/00 (2006.01)

(52) U.S. Cl.
CPC ............ A61B 6/037 (2013.01); A61B 6/5235 (2013.01); A61B 6/585 (2013.01); G06T 7/0028 (2013.01); G06T 11/60 (2013.01); G06T 2207/10104 (2013.01); G06T 2207/30004 (2013.01); G06T 2207/30204 (2013.01); G06T 2210/41 (2013.01)

(58) Field of Classification Search
CPC ....... A61B 6/037; A61B 6/5235; A61B 6/585; G06T 7/0028; G06T 11/60
See application file for complete search history.

(56) References Cited

U.S. PATENT DOCUMENTS

2012/0126125 A1* 5/2012 Akazawa ............... A61B 6/037
250/363.04

FOREIGN PATENT DOCUMENTS

WO  2007003730 A1  1/2007

* cited by examiner

*Primary Examiner* — Duy M Dang
(74) *Attorney, Agent, or Firm* — Maier & Maier, PLLC

(57) ABSTRACT

Disclosed herein is a partially movable radiation tomography apparatus capable of superimposing an anatomical image and a functional image without causing misalignment. The apparatus of the disclosure includes a device associated with a CT gantry having a top board, and a device associated with a PET gantry. The latter device is attachable and removable to/from the former device. This apparatus can reduce positional misalignment between the images captured by these devices. The present disclosure involves making a correction for positioning the subject images captured by the devices associated with the respective gantries with respect to each other based on a calibration image on which markers m attached to those gantries are shot. Such a configuration allows for positioning the subject images with possible misalignment between the gantries taken into account, and eventually reducing positional misalignment between the subject images captured by the devices associated with the respective gantries.

8 Claims, 8 Drawing Sheets

POSITIONAL RELATIONSHIP BETWEEN LINES La AND Lb

| COMPONENT OF ROTATION | COMPONENT OF ROTATION | COMPONENT OF MOVEMENT | COMPONENT OF MOVEMENT |

RADIATION TOMOGRAPHY APPARATUS

BACKGROUND

The present disclosure relates to a radiation tomography apparatus which captures a tomographic image of a subject and more particularly relates to a radiation tomography apparatus which can capture both an anatomical image and a functional image and display these images while superimposing one upon the other.

Positron emission tomography (PET) devices have been developed to capture an image representing the distribution of a radiopharmaceutical administered to a subject. A PET image captured by these PET devices is a tomographic image of the subject, and more specifically, a functional image representing an internal activity of the subject. Specifically, if a circular object is shot on a PET image, that circular part indicates the state of a particular region of the subject in which a radiopharmaceutical is distributed at a high concentration. However, the circular object shot in the PET image does not necessarily mean that the subject has a structure of the same shape as that object. In other words, the PET image is not an image representing the exact shape of, for example, an organ of the subject.

Such a state of the art poses a problem when a diagnosis is made with reference to a PET image. Specifically it is impossible, just by looking at the PET image, to accurately determine which organ of the subject has the radiopharmaceuticals at such high concentrations and exactly what part of the organ is the region of interest.

Hence, there has been proposed a technique for displaying a CT image (an MR image) and a PET image while superimposing them one upon the other. A CT image, captured with an x-ray, is called an "anatomical image." In other words, if a circular object is shot on a CT image, it means that a structure having the same shape as the circular object exists in the subject. Suppose the subject is virtually sectioned on a transverse plane of the subject, the section becomes the same as the CT image as viewed on that transverse plane. When the PET image and the CT image are displayed while being superimposed one upon the other, the superimposed image tells the user exactly which organ of the subject has the radiopharmaceuticals at such high concentrations and precisely what part of the organ is the region of interest.

The PET image and the CT image cannot be captured by the same device. Thus, it is important to accurately position these two images with respect to each other before superimposing them on upon the other. That is to say, misalignment will occur between the PET image and the CT image unless the transverse plane of the PET image is the same as the transverse plane of the CT image to be superimposed on this PET image. Such misalignment needs to be avoided to make an accurate diagnosis.

In a device that displays a PET image and a CT image while superposing them one upon the other, a PET device and a CT device are integrated together. In such a device, the positional relationship between these devices is known in advance. Thus, it is easy to capture a CT image having the same transverse plane as a PET image. The transverse planes of the CT image and PET image captured by such a device are merely spaced apart from each other by the distance between the two devices.

Another technique for displaying a CT image superimposed on a PET image includes utilizing a PET device and a CT device which are provided in two different rooms. According to such a technique, both of the devices previously execute calibration imaging in order to make correction to a sectioning position. When the images are superimposed one upon the other, the result of the calibration imaging is used to correct the imaging positions to avoid the occurrence of misalignment between the images (see International Patent Application No. WO2007/03730, for example).

However, the conventional radiation tomography apparatus has the following problem. Specifically, the conventional radiation tomography apparatus is not configured such that one of the two devices is movable with respect to the other device.

Currently, a radiation tomography apparatus is being developed which is configured such that one of a PET device and a CT device is fixed and the other is movable. Such a configuration allows for not only recombining and removing the devices according to the purpose of an inspection but also a more flexible application of the radiation tomography apparatus.

It is difficult for such a partially movable radiation tomography apparatus to capture a CT image having the same transverse plane as a PET image, and thus misalignment occurs easily between the two images. The misalignment tends to be caused due to an inconsistent distance between the two devices. This is a difference between the partially movable radiation tomography apparatus and the radiation tomography apparatus in which the CT device and the PET device are integrated together.

Moreover, it is impossible to apply as it is, to the partially movable radiation tomography apparatus, the conventional technique for correcting an imaging position between the PET device and CT device that are provided in two different rooms. In this case, the correction technique cannot be used unless the PET device and the CT device have different beds. The calibration imaging is executed with a marker placed on the bed. Here, the positional relationship between the bed and the imaging field of view of the PET device is known, and the positional relationship between the bed and the imaging field of view of the CT device is also known. In the partially movable radiation tomography apparatus, however, the positional relationship between the movable CT device and its bed is indefinite, even if the positional relationship between, for example, the PET device and the bed that are both fixed on the floor is known. Hence, a change in the positional relationship between the CT device and the PET device makes it impossible to use the correction technique involving the calibration imaging.

In view of the foregoing background, the present disclosure provides a partially movable radiation tomography apparatus which can superimpose an anatomical image and a functional image one upon the other without causing misalignment between them.

SUMMARY

In order to solve the above problems, the present disclosure is implemented in the following configuration. Specifically, a radiation tomography apparatus comprises a first gantry which has an opening to receive a subject therethrough; a top board on which the subject is placed, the top board being attached to a device associated with the first gantry; a top board mover configured to move the top board in a direction in which the opening extends with respect to the first gantry; a second gantry which is attachable and removable to/from the device associated with the first gantry, the second gantry having an opening to receive the top board on which the subject is placed; and a corrector configured to make a correction for positioning a subject image captured by the device associated with the first gantry with respect to a subject image captured by the device associated with the second gantry; wherein the corrector makes the correction for positioning the subject images based on a calibration image captured to shoot, in a single field of view, a marker attached to the first gantry and a marker attached to the second gantry.

According to the present disclosure, the radiation tomography apparatus includes a device associated with a first gantry having a top board as an attachment, and a device associated with a second gantry. The device associated with the second gantry is attachable and removable to/from the device associated with the first gantry. The radiation tomography apparatus successfully reduces positional misalignment of images captured by the respective devices. The present disclosure allows for making a correction for positioning (i) the subject image captured by the device associated with the first gantry and (ii) the subject image captured by the device associated with the second gantry with respect to each other based on a calibration image captured to shoot, in a single field of view, markers attached to the first and second gantries. Such a configuration allows for positioning the subject images with a possible misalignment of the second gantry with respect to the first gantry taken into account, thereby reducing positional misalignment between the subject image captured by the device associated with the first gantry and the subject image captured by the device associated with the second gantry.

In the radiation tomography apparatus, one of the device associated with the first gantry or the device associated with the second gantry may capture an image representing a form of the subject, and the other one of the devices captures an image representing a distribution of a pharmaceutical in the subject.

In the radiation tomography apparatus, one of the device associated with the first gantry or the device associated with the second gantry may be a radiotherapy device.

The above radiation tomography apparatus is a specific embodiment of the present disclosure. Specifically, one of the device associated with the first gantry or the device associated with the second gantry may capture an image representing the form of the subject, and the other may capture an image representing the distribution of the pharmaceutical in the subject. Such a configuration allows for precisely positioning an anatomical image and a functional image with respect to each other. Moreover, the present disclosure is also applicable to a radiation tomography apparatus in which one of the device associated with the first gantry or the device associated with the second gantry is a radiotherapy device.

In the radiation tomography apparatus, the first gantry may be provided with a holder which is configured to retain positions of a plurality of markers that are attached to the first gantry and that include the marker.

In the radiation tomography apparatus, the second gantry may be provided with a holder which is configured to retain positions of a plurality of markers that are attached to the second gantry and that include the marker.

The above radiation tomography apparatus is a specific embodiment of the present disclosure. When markers attached to the gantries are retained by the holders, the positional relationship between the markers retained by the holders does not change. This allows for sensing the positional relationship between the gantries more precisely.

In the radiation tomography apparatus, the corrector may make the correction for positioning by performing, in combination, a correction including translation of the subject image and a correction including rotation of the subject image The above radiation tomography apparatus is a specific embodiment of the present disclosure. The corrector may perform the correction for positioning by performing, in combination, a correction including translation of the subject image and a correction including rotation of the subject image. This allows for completing the correction operation more reliably.

In the radiation tomography apparatus, an optical tracker may capture the calibration image.

The above radiation tomography apparatus is a specific embodiment of the present disclosure. Providing such an optical tracker that captures the calibration image allows the radiation tomography apparatus to capture a calibration image more reliably.

In the radiation tomography apparatus, a superimposer may superimpose the subject images, on which the correction for positioning has been made, one upon the other to generate a superimposed image.

The above radiation tomography apparatus is a specific embodiment of the present disclosure. Providing such a superimposer that superimposes the subject images, on which the correction for positioning has been performed, one upon the other to generate a superimposed image allows the radiation tomography apparatus to generate such a superimposed image that facilitates diagnosis.

A radiation tomography apparatus according to the present disclosure includes a device associated with a first gantry having a top board as an attachment, and a device associated with a second gantry. The device associated with the second gantry is attachable and removable to/from the device associated with the first gantry. The radiation tomography apparatus successfully reduces positional misalignment between the images captured by the devices. The present disclosure involves making a correction for positioning subject images captured by the devices associated with the respective gantries with respect to each other, based on a calibration image representing markers attached to the respective gantries. Such a configuration allows for positioning the subject images with a possible misalignment between the respective gantries taken into account, and eventually reducing positional misalignment between the subject images captured by the devices associated with the respective gantries.

DETAILED DESCRIPTION

Embodiments

<Configuration of Radiation Tomography Apparatus>

Figure 1:
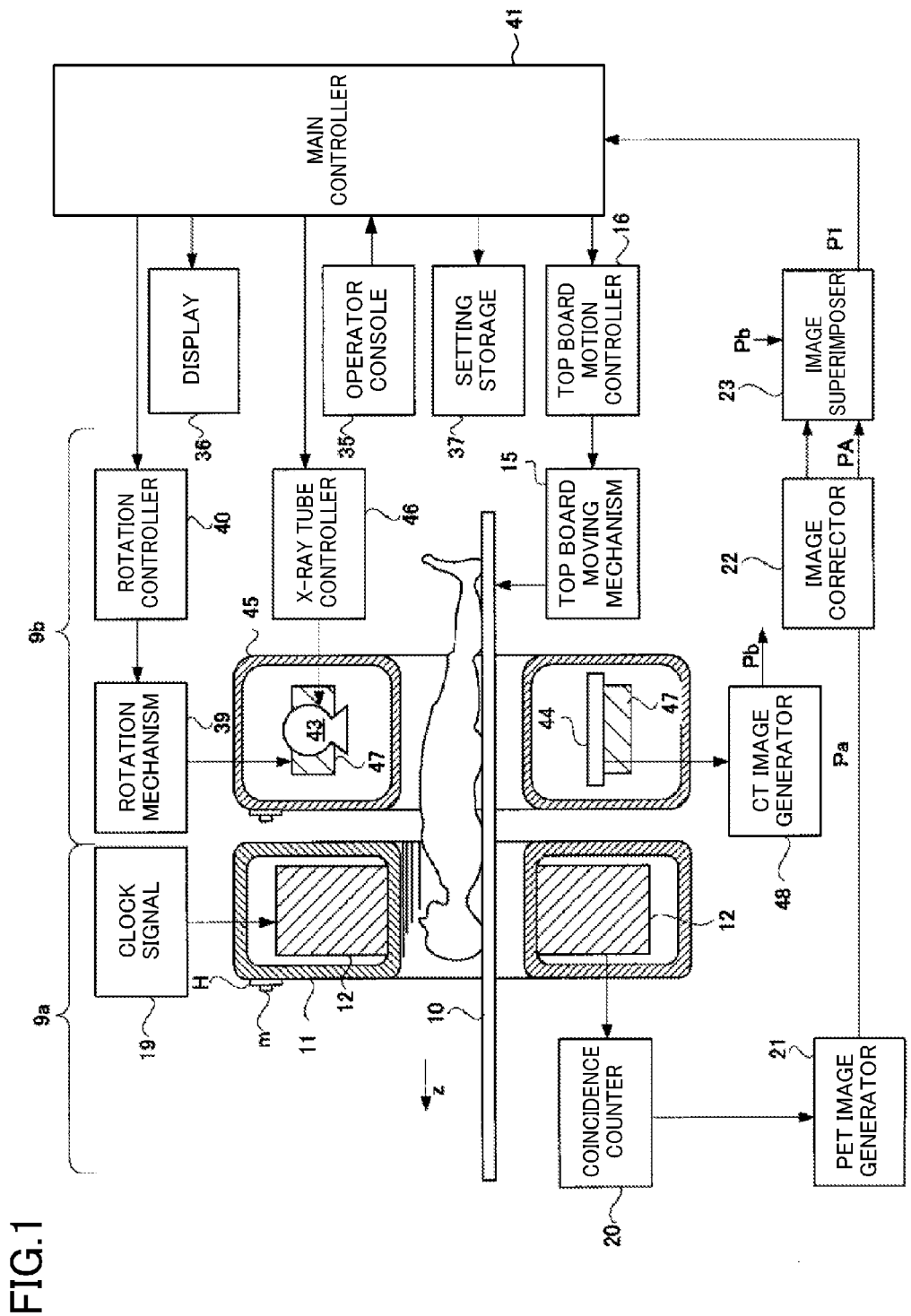
FIG. 1 is a functional block diagram illustrating the overall configuration of a radiation tomography apparatus according to an embodiment.

An embodiment of a radiation tomography apparatus according to the present disclosure will now be described with reference to the drawings. A gamma ray and an x-ray according to an embodiment are exemplary radiations of the present disclosure. FIG. 1 is a functional block diagram illustrating a configuration for a radiation tomography apparatus according to an embodiment. The radiation tomography apparatus of this embodiment is a PET/CT apparatus including a CT device 9b and a PET device 9a.

Figure 2:
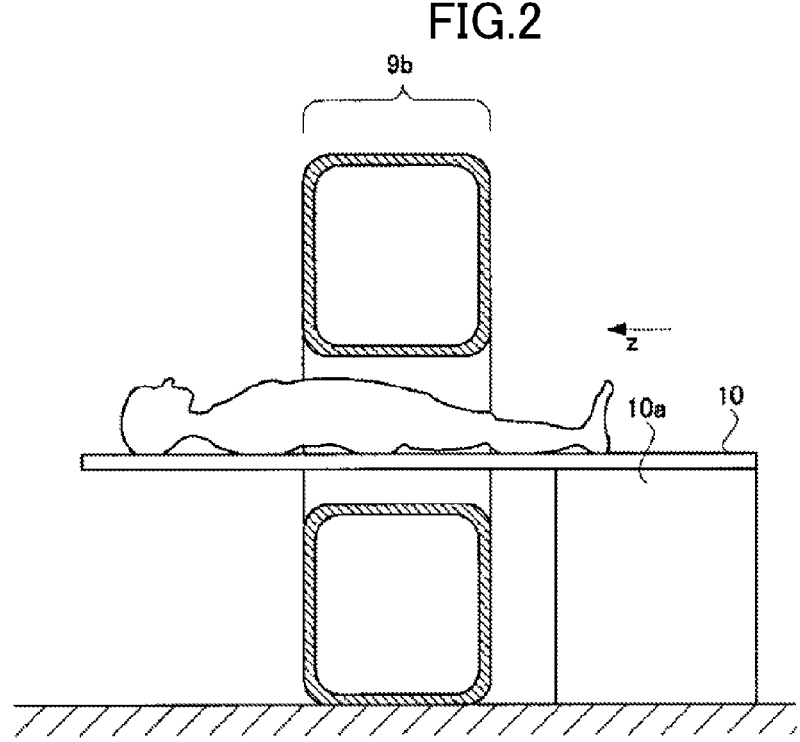
FIG. 2 is a cross-sectional view illustrating a configuration for a PET device according to an embodiment.

The PET/CT apparatus according to this embodiment may also capture an image using the CT device 9b alone. That is to say, the PET device 9a that forms part of this PET/CT apparatus may be removed from the CT device 9b such that an image may be captured using the CT device alone. Alternatively, an image may also be captured using the PET device 9a and the CT device 9b in combination. FIG. 2 illustrates such a state where the PET device 9a has been removed from the CT device 9b. The CT device 9b is fixed on the floor of an inspection room. A top board 10 is an attachment of the CT device 9b. If the imaging is carried out using the apparatus shown in FIG. 2, the CT scanning is not interfered with by the PET device 9a, and therefore, can be carried out smoothly. A PET gantry 11 is attachable and removable to/from a device associated with a CT gantry 45. The PET device 9a is designed to capture an image representing the distribution of a pharmaceutical in the subject, and the CT device 9b is designed to capture an image representing the form of a subject M.

Figure 3:
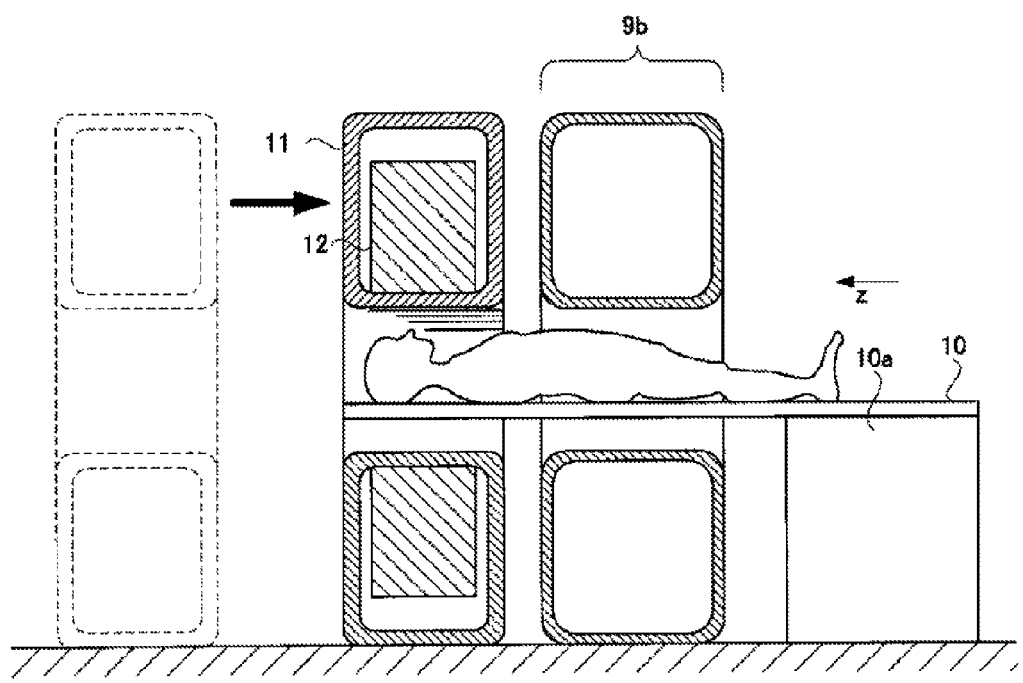
FIG. 3 is a cross-sectional view illustrating a configuration for a CT device according to an embodiment.

FIG. 3 illustrates a state where the PET device 9a is going to be attached to the CT device 9b. The PET device 9a has casters to allow the device to roll on the inspection room floor. When the image is being shot, the casters of the PET device 9a are locked such that the positional relationship between the CT device 9b and the PET device 9a is maintained. If the PET device 9a is brought closer to the CT device 9b as indicated by the arrow in FIG. 3, the imaging may be carried out by using this apparatus as a PET/CT apparatus capable of performing both PET imaging and CT imaging. If an image is shot using the apparatus shown in FIG. 3, the imaging operation allows for capturing not only an anatomical image by the CT device 9b but also a functional image by the PET device 9a.

Note that, for the convenience of description, the PET gantry 11 included in the PET device 9a and the CT gantry 45 included in the CT device 9b have the same size and shape when viewed in the z-direction. The CT gantry 45 and the PET gantry 11 are respectively equivalent to a first gantry and a second gantry of the present disclosure.

<Configuration of CT Device>

Described next is a configuration for the CT device 9b according to this embodiment. As illustrated in FIG. 1, the CT device 9b includes the top board 10 on which the subject M is placed, and the CT gantry 45 having an opening receiving the top board 10 and the subject M in the longitudinal direction thereof (i.e., the z-direction). The opening of the CT gantry 45 extends in the z-direction, and the top board 10 and the subject M are received through the opening. As can be seen, the top board 10 is an attachment of the CT device 9b. A base 10a which supports the top board 10 is also an attachment of the CT device 9b. The base 10a is fixed on the inspection room floor.

Inside the CT gantry 45, provided are an x-ray tube 43 which emits an x-ray toward the subject M, an x-ray detector 44 which detects the x-ray transmitted through the subject M, and a support 47 which supports the x-ray tube 43 and the x-ray detector 44. The support 47 has a ring shape and is rotatable about the z-axis. The support 47 is rotated by a rotation mechanism 39 including, for example, a power generator such as a motor and a power transmission unit such as a gear. A rotation controller 40 controls this rotation mechanism 39. The central axis of rotation of the support 47 (i.e., the x-ray tube 43 and the x-ray detector 44) agrees with the central axis of a detector ring 12 in the PET device 9a. The detector ring 12 will be described later. That is to say, the CT device 9b, of which the central axis agrees with that of the detector ring 12, is provided adjacent to the PET device 9a in the z-direction. The x-ray tube 43 and the x-ray detector 44 are respectively equivalent to a radiation source and a radiation detector of the present disclosure.

A CT image generator 48 generates an x-ray anatomical tomographic image (i.e., a CT image Pb) of the subject M based on the x-ray detection data output from the x-ray detector 44. This CT image Pb is a 3D image of the subject M, and indicates the degree of x-ray permeability inside the subject M. The CT image generator 48 is equivalent to a tomographic image generator of the present disclosure.

The top board 10 is slidably provided in the z-direction to penetrate the opening of the CT gantry 45 in the z-direction. Such a sliding motion of the top board 10 may be set up by a top board moving mechanism 15. The top board moving mechanism 15 is controlled by a top board motion controller 16. The top board motion controller 16 controls the top board moving mechanism 15. This top board motion controller 16 is configured to move the top board 10 with respect to the CT gantry 45 in the direction in which the opening extends. The entire top board 10 may slide from a position outside of the CT gantry 45 to be introduced into the opening of the CT gantry 45 from one side thereof, and go through the inside of the CT gantry 45 to project from the other side of the opening of the CT gantry 45.

<Configuration of PET Device>

Described first is a configuration for the PET device 9a. The PET device 9a includes the PET gantry 11 having an opening to receive the subject M in the longitudinal direction (i.e., the z-direction) of the subject M, and the detector ring 12 provided inside the PET gantry 11 and having a ring shape. The opening of the detector ring 12 is cylindrical and extending in the z-direction (i.e., the longitudinal direction of the top board 10 and the superior-inferior (body axis) direction of the subject M). The detector ring 12 is equivalent to a detector of the present disclosure. Note that the PET device 9a is adjacent to the CT device 9b in the z-direction. The PET gantry 11 of the PET device 9a and the CT gantry 45 of the CT device 9b are arranged such that their openings are in contact with each other in the z-direction. Such an arrangement allows for continuously capturing a CT image Pb and a PET image Pa while minimizing a change in the position of the subject M on the top board 10. The detector ring 12 detects an annihilation gamma ray to be generated in the subject. Note that the top board moving mechanism 15 and the positional relationship between the PET gantry 11 and the CT gantry 45 according to this embodiment are merely exemplary specific implementations that may be adopted. Hence, the configuration of the present disclosure shall not be limited to these specific implementations.

Inside the PET gantry 11, provided is the detector ring 12 that detects the annihilation gamma ray radiated from the subject M. This detector ring 12 is configured as a cylinder extending in the superior-inferior direction of the subject M, and has a length of approximately 15 cm to 30 cm in the z-direction. A clock signal 19 is input to the detector ring 12. Time information, indicating a point in time when the gamma ray was detected is added, responsive to the clock signal 19, to the detection data output from the detector ring 12. Then the detection data is input to a coincidence counter 20 which will be described later.

The coincidence counter 20 determines whether the detection data provided by the detector ring 12 are coincident events. Note that the time information added to the detection data responsive to the clock signal 19 is used by the coincidence detector 20 to make decision on the coincidence of the detection data. The coincidence counter 20 recognizes two gamma rays, which have been sensed to have entered the detector ring 12 simultaneously, to be annihilation gamma rays radiated due to the presence of a radiopharmaceutical in the subject, and transmits the detection data on the two gamma rays to a PET image generator 21.

The PET image generator 21 generates a PET image Pa based on the detection data output from the detector ring 12 via the coincidence counter 20. This PET image Pa is a 3D image of the subject M, and represents the intensity of the annihilation gamma ray generated. An image superimposer 23 is provided to generate a superimposed image P1.

Described next is a configuration for the detector ring 12. According to this embodiment, approximately 100 radiation detectors 1 are arranged in a virtual circle on a plane perpendicular to the z-direction, thereby forming a single unit ring. A number of such unit rings are arranged in the z-direction to form the detector ring 12.

Figure 4:
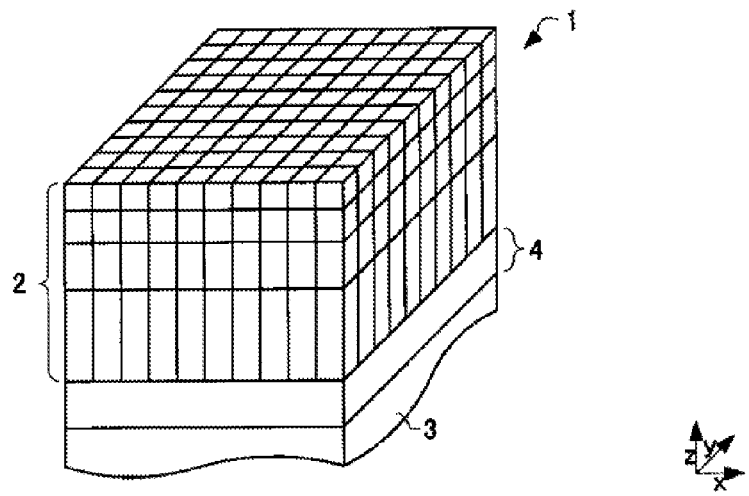
FIG. 4 is a perspective view illustrating a configuration for a PET device according to an embodiment.

Briefly described next is a configuration for a radiation detector 1. FIG. 4 is a perspective view illustrating a configuration for the radiation detector 1 according to this embodiment. As illustrated in FIG. 4, the radiation detector 1 includes a scintillator 2 which transforms a gamma ray into fluorescence, and a photodetector 3 which detects the fluorescence. Provided between the scintillator 2 and the photodetector 3 is a light guide 4 which receives the fluorescence and guides it to the photodetector 3.

The scintillator 2 is comprised of scintillator crystals that are arranged three-dimensionally. A scintillation crystal is made of $Lu_{2(1-x)}Y_{2x}SiO_5$ in which Ce is diffused (hereinafter referred to as "LYSO"). The photodetector 3 is designed to locate a fluorescence generation position indicating which scintillator crystal has generated the fluorescence. The photodetector 3 is also designed to detect the intensity of the fluorescence, and a time when the fluorescence was generated. Furthermore, the scintillator 2 according to this embodiment is merely an exemplary implementation that may be adopted. Hence, the configuration of the present disclosure shall not be limited to this particular implementation.

Note that the PET device 9a includes a main controller 41 which performs overall control of the respective units, and a display 36 which displays images such as an anatomical tomographic image thereon. This main controller 41 is configured as a central processing unit (CPU) and executes various programs to perform the functions of not only the units 16, 20, 21, 22, 23, and 24, but also units 25 and 26 which will be described later. Note that each of these units may be implemented separately in the form of a control device in charge of the function assigned to itself.

A setting storage 37 stores various parameters regarding the inspection. An operator console 35 allows the operator to input various operation parameters. The operator console 35 is equivalent to an input unit of the present disclosure.

The PET image Pa generated by the PET image generator 21 and the CT image Pb generated by the CT image generator 48 are 3D images representing the same region of the subject M on the same transverse section at the same zoom power. The difference between the two images is that the CT image Pb represents the internal body structure of the subject M, whereas the PET image Pa represents the distribution of a radiopharmaceutical there.

The main controller 41 executes various programs to perform the functions of not only the respective units associated with the PET device 9a, but also the rotation controller 40, the CT image generator 48, and an x-ray tube controller 46. Note that each of these units may be implemented separately in the form of a control device in charge of the function assigned to itself. The x-ray tube controller 46 controls a tube current, a tube voltage, a pulse width and other parameters of the x-ray tube 43.

<Marker>

Figure 5:
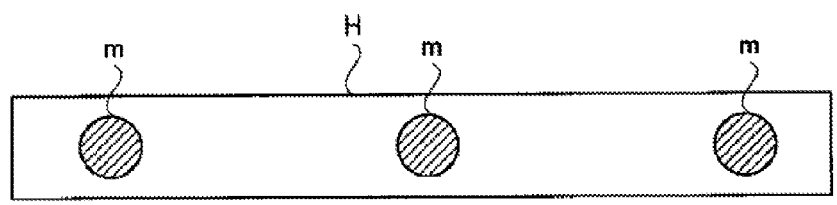
FIG. 5 is a plan view illustrating an arrangement of markers according to an embodiment.
Figure 6:
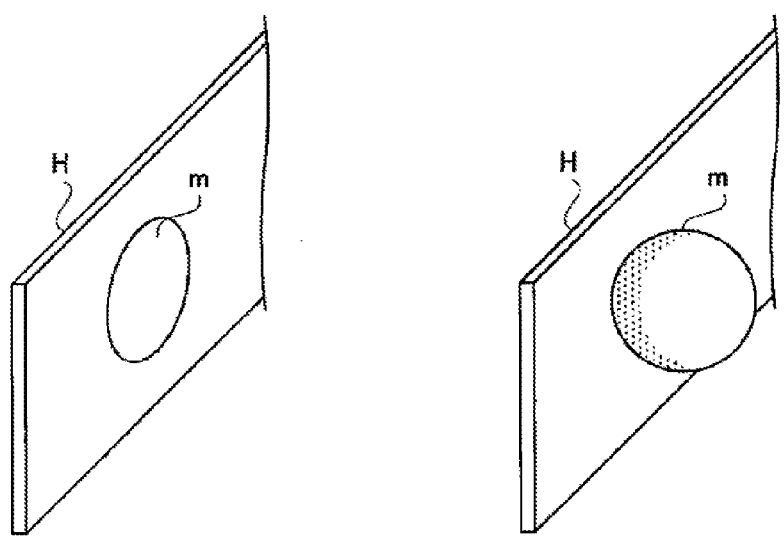
FIG. 6 is a perspective view illustrating the configuration of a marker according to an embodiment.

Described below is a marker m, which is used by the radiation tomography apparatus according to the present disclosure to indicate a relative position of the PET device 9a with respect to the CT device 9b. The marker m is a circular one as illustrated in FIG. 5, and attached to an elongate holder H. Three markers m are attached to the holder H and arranged in line in the direction in which the holder H extends. Furthermore, the marker m may be a structure in the form of a sticker as illustrated in FIG. 6 on the left side of the paper. Alternatively, the marker m may also be a spherical structure as illustrated in FIG. 6 on the right side of the paper. The marker m does not have to be a circular or spherical one but may be, for example, a crisscross one. The number of the markers m to be attached to the holder H does not have to be three but may also be two or more than three. The positional relationship between these markers m does not change, since these markers m are attached to the holder H.

Figure 7:
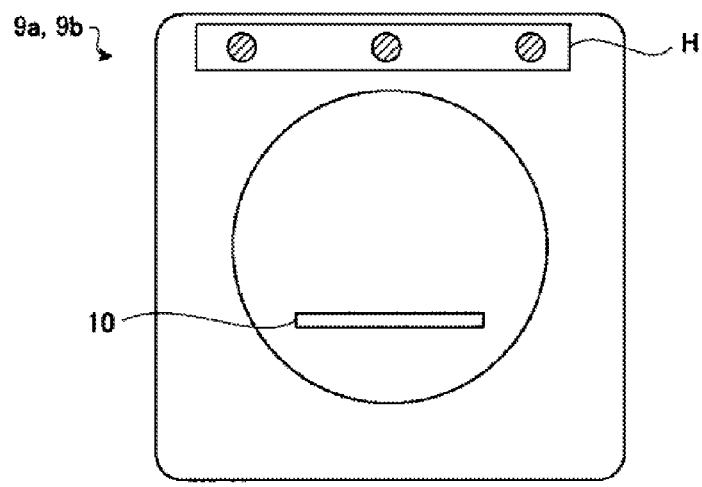
FIG. 7 is a plan view illustrating how to attach a marker according to an embodiment.

FIG. 7 illustrates how the markers m are provided to a gantry of the device. As shown in FIG. 7, the holder H is secured to an upper portion of a side face of the gantry 11, 45. The holder H is attached to a side face of the gantry 11, 45 and positioned above the opening of that side face for receiving the subject. Specifically, the holder H is attached to a portion of the side face immediately above the opening such that the markers m are arranged parallel to the upper side of the side face of the gantry 11, 45. The upper side of the side face of the gantry 11, 45 is one of the four sides of the side face of the gantry 11, 45 that is located farther away from the floor than any other side thereof. The side faces of the gantries 11 and 45 have the same shape, and the holders H are secured to the same position on the gantries 11 and 45. The holders H secured to the gantries 11 and 15 are identical ones. Hence, each of the gantries 11 and 45 has three markers m attached thereto. That is to say, a holder H, retaining the positions of multiple markers m to be attached to the PET gantry 11, is provided for the PET gantry 11, and another holder H, retaining the positions of multiple markers m to be attached to the CT gantry 45, is provided for the CT gantry 45.

<Optical Tracker>

Figure 8:
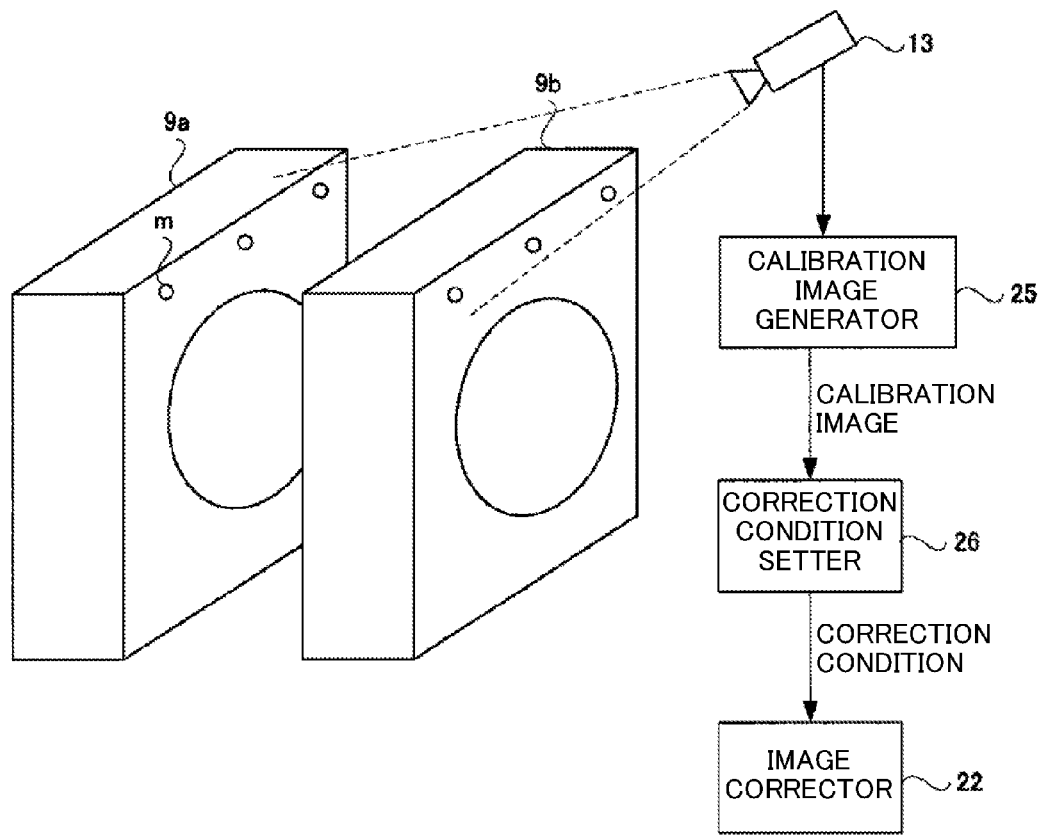
FIG. 8 is a perspective view illustrating how to capture a marker according to an embodiment.

The radiation tomography apparatus according to the present disclosure includes an optical tracker 13 which captures the markers m using a visible ray. As shown in FIG. 8, the optical tracker 13 is provided above the gantries 11 and 45, and captures six markers m using a visible ray such that three of the six markers m attached to the PET gantry 11 and the other three markers m attached to the CT gantry 45 are shot within the same field of view. When the optical tracker 13 captures an image, the captured image data output by the optical tracker 13 is transmitted to a calibration image generator 25. The calibration image generator 25 generates a calibration image based on the captured image data. The optical tracker 13 includes two cameras which are integrated together to have mutually different viewpoints and synchronized capturing timing. The optical tracker 13 is configured to capture two images to produce a stereoscopic image. Hence, when capturing the images of the six markers m, the optical tracker 13 outputs image data captured by a first camera and image data captured by a second camera. The calibration image generator 25 generates two calibration images corresponding to the two sets of image data captured. The optical tracker 13 is equivalent to an optical tracker of the present disclosure.

Hence, when the markers m are attached to the side faces of the gantries 11 and 45, the markers m need to be positioned such that the optical tracker 13 can capture an image of all of these markers m. Specifically, the makers m are attached to the gantries 11 and 45 so as not to be located on the back of the gantry 11 or 45, or hidden behind the front gantry 11 or 45 when viewed from the optical tracker 13. If three markers m are attached to a side face of the PET gantry 11 which is located closer to the base 10a supporting the top board 10, the other three markers m are also attached to a corresponding side face of the CT gantry 45 which is located closer to the base 10a. On the other hand, if three markers m are attached to a side face of the PET gantry 11 which is located farther away from the base 10a, the other three markers m are also attached to a corresponding side face of the CT gantry 45 which is located farther away from the base 10a.

<Correction Condition Calculator>

The two calibration images thus generated are then transmitted to a correction condition calculator 26. Based on the two calibration images, this correction condition calculator 26 calculates a correction condition indicating specifically how to position the PET image Pa and the CT image Pb when the images are superimposed one upon the other. Described below in detail is an operation of the correction condition calculator 26.

Figure 9:
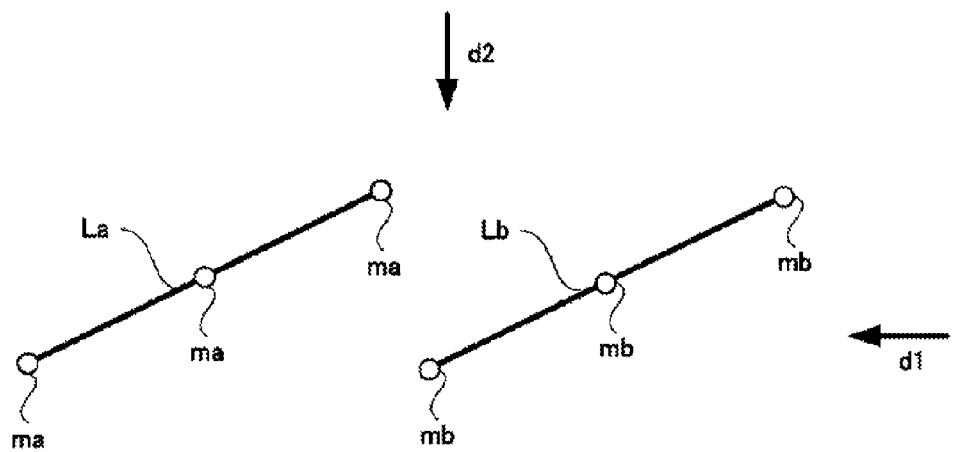
FIG. 9 is a schematic representation illustrating how to calculate a correction condition according to an embodiment.

The correction condition calculator 26 determines a stereoscopic positional relationship between a line segment La and a line segment Lb based on the two calibration images captured from two different viewpoints. Here, the line segment La connect together the three markers ma attached to the CT gantry 45, and the line segment Lb connects together the three markers mb attached to the PET gantry 11. FIG. 9 schematically illustrates the two line segments La and Lb recognized by the correction condition calculator 26. As shown in FIG. 9, suppose the direction d1 is the direction pointing from one line segment Lb to the other line segment La, and the direction d2 is the direction perpendicular to a plane including these line segments La and Lb. The correction condition calculator 26 stores the positional relationship thus recognized between the line segments La and Lb in the form of a three-dimensional map. The line segment La is drawn by connecting together the centroids of the respective markers ma on the three-dimensional map, and the line segment Lb is drawn by connecting together the respective centroids of the markers mb on the three-dimensional map.

Figure 10:
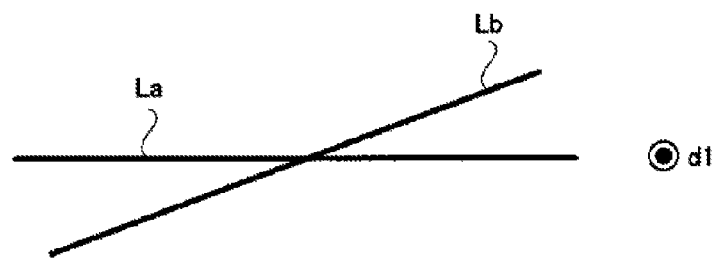
FIG. 10 is a schematic representation illustrating how to calculate a correction condition according to an embodiment.
Figure 11:
FIG. 11 is a schematic representation illustrating how to calculate a correction condition according to an embodiment.

The line segments La and Lb neither intersect nor overlap with each other. The line segment La indicates the installation direction and location of the CT gantry 45, and the line segment Lb indicates the installation direction and location of the PET gantry 11. Thus, these line segments La and Lb are always separated from each other. Nevertheless, it does not necessarily mean that the line segment Lb is perfectly parallel to the line segment La. The reason is that it is difficult to move the PET gantry 11 to an exactly fixed position with respect to the CT gantry 45. Actually, the line segment Lb would rotate, with respect to the line segment La, either (i) about a central axis parallel to the direction d1, or (ii) about a central axis parallel to the direction d2. FIG. 10 illustrates a rotation of the line segment Lb with respect to the direction d1. FIG. 11 illustrates a rotation of the line segment Lb with respect to the direction d2.

Furthermore, the line segments La and Lb are misaligned from each other in the direction d1. This misalignment is caused because the CT gantry 45 and the PET gantry 11 are arranged side by side in the z-direction as shown in FIG. 1. Thus, such an arrangement causes significant the misalignment. The degree of this misalignment is not necessarily constant every time the PET gantry 11 is placed with respect to the CT gantry 45. This is because it is difficult to move the PET gantry 11 to an exactly fixed position with respect to the CT gantry 45.

Besides, these line segments La and Lb are also misaligned from each other with respect to the direction perpendicular to the directions d1 and d2. In FIG. 9, this is misalignment in the direction pointing to an upper right corner of the paper. The degree of misalignment of the gantries in this direction is insignificant compared with the misalignment in the direction d1. However, it is difficult to completely eliminate the misalignment in that direction. This is because it is difficult to move the PET gantry 11 to an exactly fixed position with respect to the CT gantry 45.

The correction condition calculator 26 calculates the degree of rotation and translation of the line segment Lb with respect to the line segment La based on the three-dimensional map representing the positional relationship between the line segments La and Lb. The correction condition calculator 26 breaks down the positional relationship between the line segments La and Lb into four components, namely, a component of rotation illustrated in FIG.

Figure 12:
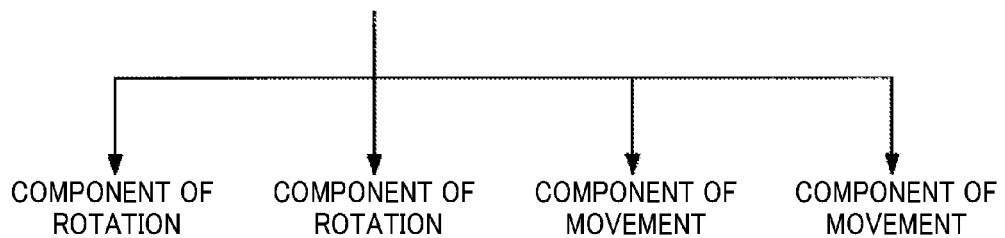
FIG. 12 is a schematic representation illustrating how to calculate a correction condition according to an embodiment.

10, a component of rotation illustrated in FIG. 11, a component of movement in the direction d1, and a component of movement in the direction perpendicular to the directions d1 and d2. The correction condition calculator 26 then calculates the degrees of rotation and movement for each of the line segments La and Lb. FIG. 12 schematically illustrates how the correction condition calculator 26 breaks down the positional relationship between the line segments La and Lb into the four components.

In calculating the degree of rotation in relation to the direction d1, the correction condition calculator 26 projects the line segments La and Lb to a plane which intersects with the direction d1 at right angles, generates an image in which the line segments La and Lb intersects with each other as shown in FIG. 10, and then calculates the angle formed between the line segments La and Lb. This angle represents the degree of rotation in relation to the direction d1. Likewise, in calculating the degree of rotation in relation to the direction d2, the correction condition calculator 26 projects the line segments La and Lb to a plane which intersects with the direction d2 at right angles, generates an image as shown in FIG. 11, and calculates the angle formed between two lines which are extensions of the line segments La and Lb. This angle represents the degree of rotation in relation to the direction d2.

In capturing the component of movement in the direction d1 and the component of movement in the direction perpendicular to the directions d1 and d2, the correction condition calculator 26 first makes correction to the line segment Lb, based on the degrees of rotation described above, such that the line segment Lb rotates with respect to the line segment La, and places the line segments La and Lb parallel to each other. The correction condition calculator 26 then calculates in what direction and how much the centroids of the line segments La and Lb have moved. The component of movement in the direction d1 having the degree thus calculated is the component of movement in the direction d1 described above. Meanwhile, the component of movement in the direction perpendicular to the directions d1 and d2 that has been calculated in this manner is the component of movement in the direction perpendicular to the directions d1 and d2 described above.

The correction condition calculator 26 transmits the degrees of rotation and movement thus calculated to the setting storage 37, and makes the setting storage 37 store those values. These degrees of rotation and movement become parameters that need to be used in positioning the PET image Pa and the CT image Pb when these images are superimposed one upon the other.

Figure 13:
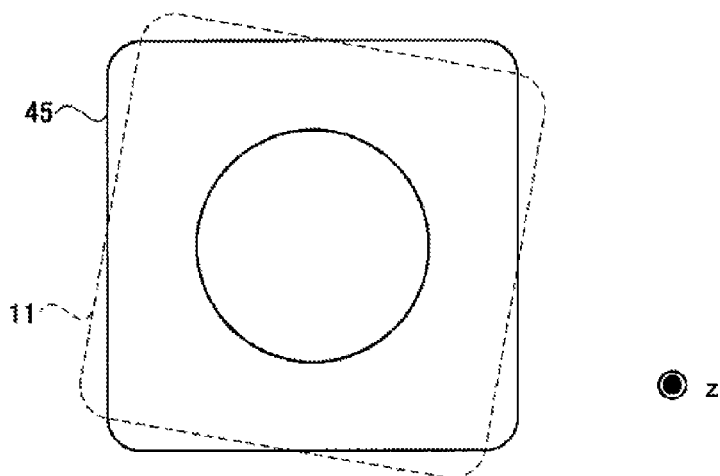
FIG. 13 is a schematic representation illustrating how misalignment occurs between devices according to an embodiment.

For example, the degree of rotation in the direction d1, calculated by the correction condition calculator 26, indicates as illustrated in FIG. 13 how much the PET gantry 11 has rotated with respect to the CT gantry 45 about an axis extending in the z-direction as its axis of rotation. Ideally, the CT gantry 45 and the PET gantry 11 are arranged to overlap with each other when observed from the z-direction. However, it is difficult to arrange the PET gantry 11 at such an ideal position when the PET gantry 11 is placed with respect to the CT gantry 45.

Figure 14:
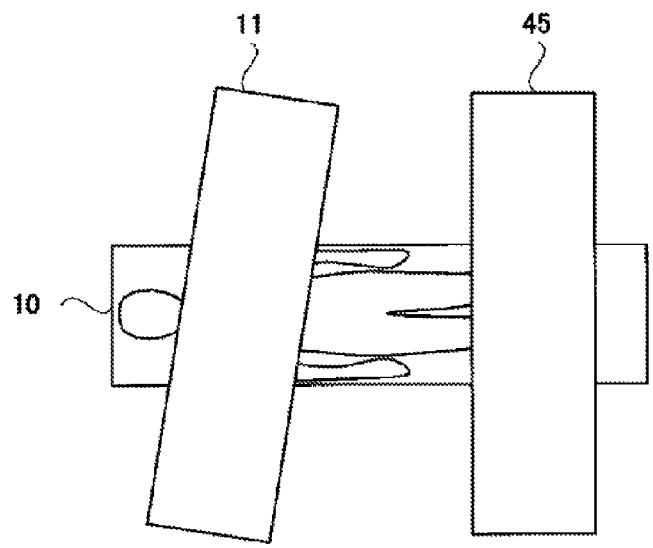
FIG. 14 is a schematic representation illustrating how misalignment occurs between the devices according to an embodiment.

Furthermore, the degree of rotation in the direction d1, calculated by the correction condition calculator 26, indicates how much the PET gantry 11 tilts with respect to the CT gantry 45 about an axis extending in the vertical direction as its axis of rotation. FIG. 14 schematically illustrates a tilt in such a situation. Ideally, the CT gantry 45 and the PET gantry 11 are arranged parallel to each other when viewed vertically downward. However, it is difficult to arrange the PET gantry 11 at such an ideal position when the PET gantry 11 is placed with respect to the CT gantry 45.

Figure 15:
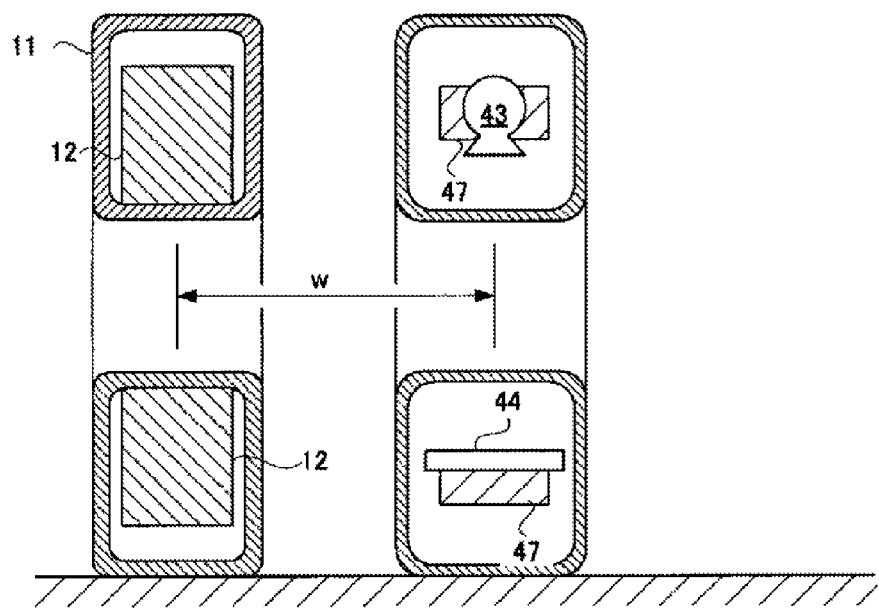
FIG. 15 is a schematic representation illustrating how misalignment occurs between images according to an embodiment.

The degree of movement calculated by the correction condition calculator 26 indicates how much the PET gantry 11 has shifted with respect to the CT gantry 45. Specifically, the component of movement in the direction d1 calculated by the correction condition calculator 26 indicates how far the gantries 11 and 45 are spaced apart from each other in the z-direction. The component of movement in the direction perpendicular to the directions d1 and d2, calculated by the correction condition calculator 26, indicates how much the gantries 11 and 45 are misaligned from each other in the direction perpendicular to the z-direction and the vertical direction. Ideally, as illustrated in FIG. 15, the PET gantry 11 is spaced apart from the CT gantry 45 by a predetermined shift width w in the z-direction, and is not misaligned with the CT gantry 45 in the direction going into the paper (i.e., in the lateral direction of the subject M) in FIG. 15. However, it is difficult to arrange the PET gantry 11 at such an ideal position when the PET gantry 11 is placed with respect to the CT gantry 45.

This shift width w is the distance between the centers respectively defined for the gantries 11 and 45. As used herein, the "center of a gantry" refers to the center of the field of view of the device.

As can be seen, the correction condition calculator 26 calculates the degree of misalignment of the PET gantry 11 with respect to the CT gantry 45 by analyzing the three-dimensional map on which the markers m are shot. The result of calculation captured by the correction condition calculator 26 will be hereinafter referred to as a "correction condition." The correction condition includes a condition on the degrees of two kinds of rotation and a condition on the degrees of two kinds of translation.

<Image Corrector>

The correction condition calculated by the correction condition calculator 26 is transmitted to an image corrector 22. In accordance with the correction condition, the image corrector 22 corrects the position of the PET image Pa provided by the PET device 9a. The image corrector 22 is equivalent to a corrector of the present disclosure.

The CT image Pb is voxel data on which a 3D image of the subject M is captured as described above. This CT image Pb is captured with the top board 10 moved in the z-direction. The subject M placed on the top board 10 is too long to be shot within the imaging field of view of the CT device 9b. Hence, the CT device 9b continuously captures image shots of the subject M while moving the subject M in the z-direction, and merges together the image shots thus captured to generate a 3D image of the entire body of the subject. In other words, the top board 10 needs to be moved to capture the CT image Pb. In generating the CT image Pb, the magnitude of movement of the top board 10 is also taken into account. Specifically, in the CT imaging, the CT device 9b has received data from the top board motion controller 16, with data about the magnitude of movement of the top board 10. During the imaging, the CT device 9b generates a 3D image while detecting changing positions of the subject M in the z-direction based on the data provided by the top board motion controller 16. If no data were provided by the top board motion controller 16, then the CT device 9b could not sense the motion of the subject M in the z-direction during the imaging. As a result, the only image the CT device 9b could capture in that case would be an image representing the head, chest, abdomen, and legs of the subject M overlapping with one another in the imaging field of view.

The same can be said about the PET image Pa in the form of voxel data. The PET device 9a also captures image shots of the subject M continuously while moving the subject M in the z-direction by moving the top board 10 during the imaging, and merges together the image shots thus captured to generate a 3D image of the entire body of the subject. Specifically, during the PET imaging, the PET device 9a is provided, by the top board motion controller 16, with data about the magnitude of movement of the top board 10. During the PET imaging, the PET device 9a generates a 3D image while detecting changing positions of the subject M in the z-direction based on the data provided by the top board motion controller 16.

Figure 16:
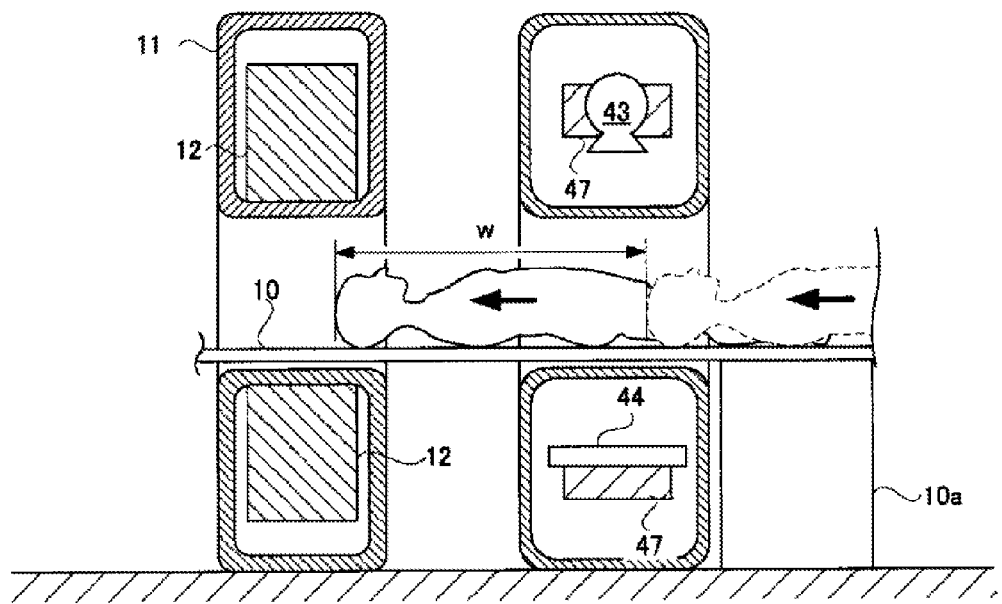
FIG. 16 is a schematic representation illustrating how misalignment occurs between images according to an embodiment.

Described below is how the subject M is moved to capture an image. The subject M in the solid profile in FIG. 16 represents the position of the subject M at a point in time when a PET image Pa starts to be captured. With the progress of the PET imaging, the subject M gradually moves toward the left of the paper as indicated by the arrows. Then, the PET imaging is completed when the toes of the subject M are captured.

If the CT device 9b is supposed to capture a CT image Pb of the entire body of the subject M after the PET device 9a has obtained a PET image Pb thereof, the top board 10 is moved before starting the capture of the CT image Pb. The subject M shown in phantom in FIG. 16 represents the position of the subject M when a CT image Pb starts to be captured. With the progress of the CT imaging, the subject M is gradually moved toward the left of the paper as indicated by the arrows. Then, the CT imaging is completed when the toes of the subject M are captured.

Hence, the position of the subject M during the CT imaging has been shifted from the position of the subject M during the PET imaging, by the shift width w shown in FIG. 15, in the direction pointing from the PET device 9a toward CT device 9b. Shifting the position of the subject M by the shift width w during the CT imaging allows the CT device 9b to capture the entire body of the subject M reliably.

Note that if there is a difference in the size of the imaging field of view between the PET device 9a and the CT device 9b, the position of the subject M at the beginning of the CT imaging does not have to be shifted by the shift width w from its position during the PET imaging. Even so, the position of the subject M during the CT imaging is still determined, based on the shift width w between the devices 9a and 9b, with reference to the position of the subject M during the PET imaging. That is to say, in that case, the CT imaging is started after the subject M has been moved by the sum of the shift width w and a predetermined distance from its position during the PET imaging. In the following description, the size of the imaging field of view is supposed to be the same between the PET device 9a and the CT device 9b, and the position of the subject M at the beginning of the CT imaging is supposed to be shifted by the shift width w from its position during the PET imaging.

As can be seen from the foregoing description, the position of the subject M during the CT imaging has been shifted by the shift width w from the position of the subject M during the PET imaging. Hence, if image processing is performed on the PET image Pa such that the subject M of the PET image Pa is moved by the shift width w toward the CT device 9b, the subject M shot in the CT image Pb and the subject M shot in the PET image Pa should exactly match each other. Actually, however, that is not the case. This is because the positional relationship between the CT image Pb and the PET device 9a during imaging is not ideal. Specifically, during the imaging, the PET device 9a might be tilted with respect to the CT device 9b as already described with reference to FIGS. 13 and 14, or might have been translated from an ideal position.

Thus, the image corrector 22 makes an image correction to the PET image Pa so as to cancel such a positional displacement of the subject image due to the misalignment between the two devices. That is to say, based on the correction condition calculated by the correction condition calculator 26, the image corrector 22 rotates and translates the subject image in the PET image Pa to capture a subject image generated by the PET device 9a that is ideally positioned with respect to the CT device 9b. An ideally positioned PET image Pa is not tilted with respect to the CT device 9b, is spaced apart by the shift width w in the z-direction, and is not shifted in the depth direction (i.e., the lateral direction of the subject M) in FIG. 1. The image corrector 22 carries out the correction for positioning by performing, in combination, a correction including translation of the subject image and a correction including rotation of the subject image.

As can be seen, the image corrector 22 performs a correction for positioning a subject image captured by a device associated with the PET gantry 11 and a subject image captured by a device associated with the CT gantry 45 with respect to each other. Specifically, the image corrector 22 performs the correction for positioning the subject images based on a calibration image captured to shoot, in a single field of view, a marker m attached to the PET gantry 11 and a marker m attached to the CT gantry 45. A PET image subjected to such correction processing by the image corrector 22 will be hereinafter referred to as a "PET image PA."

<Image Superimposer>

The image superimposer 23 superimposes the CT image Pb and the corrected PET image PA one upon the other to capture a superimposed image P1. Here, a subject image shot in the corrected PET image PA has shifted, by the shift width w, in the direction pointing from the CT device 9b toward the PET device 9a, with respect to a subject image shot in the CT image Pb. Hence, before superimposing the CT image Pb and the PET image PA one upon the other, the image superimposer 23 positions these two images with respect to each other by performing image processing on the PET image PA such that the PET image PA is shifted by this shift width w. In this manner, the image superimposer 23 superimposes the subject images one upon the other to generate a superimposed image P1. The image superimposer 23 is equivalent to a superimposer of the present disclosure.

Figure 17:
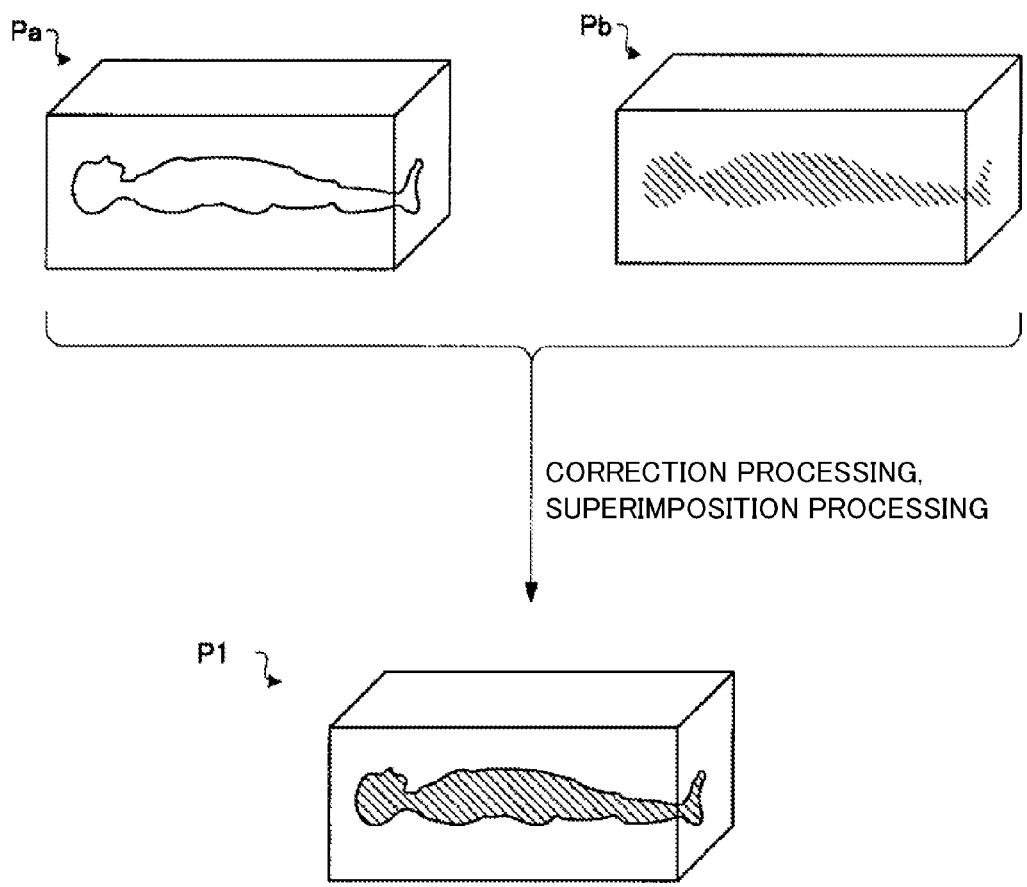
FIG. 17 is a schematic representation illustrating image processing according to an embodiment.

FIG. 17 schematically illustrates processing performed by the image corrector 22 and the image superimposer 23. After having had such influence of misalignment between the positions of the two shooting devices canceled by the image corrector 22, the PET image Pa is superimposed on the CT image Pb. This is how a superimposed image P1 is generated.

<Operation of Radiation Tomography Apparatus>

Described next is how the radiation tomography apparatus according to the embodiment operates. First, the subject M is placed on the top board 10. When the operator enters, via the operator console 35, an instruction to capture a PET image Pa, the top board 10 moves and the subject M enters the PET gantry 11. The subject M has been injected in advance with a radiopharmaceutical, which generates an annihilation gamma ray. In this manner, the annihilation gamma ray generated in the body of the subject M is detected by the detector ring 12. The detector ring 12 transmits the detection data thus captured to the coincidence counter 20, which determines whether or not the detection data thus captured are coincident events. Note that the detection data is a set of mutually related data including the time of incidence time and energy.

The detection data recognized by the coincidence counter 20 as coincident events are transmitted to the PET image generator 21. In response, the PET image generator 21 generates a PET image Pa, which is not only a tomographic image captured by sectioning the subject M on multiple planes arranged at predetermined intervals, but also an image representing three-dimensionally how the annihilation gamma ray has been generated. The image corrector 22 corrects the position of the PET image Pa in accordance with the correction condition that has been defined in advance before imaging. In this manner, a corrected PET image PA is generated.

When the operator enters, via the operator console 35, an instruction to start capturing a CT image Pb after the PET image Pa has been captured, the top board 10 moves and the subject M enters the CT gantry 45. Then, the x-ray tube 43 and the x-ray detector 44 rotate on the z-axis with their relative positions maintained.

When the operator enters, via the operator console 35, an instruction to start radiating the x-ray, the x-ray tube 43 intermittently radiates an x-ray toward the subject M. The CT image generator 48 generates an x-ray fluoroscopic image every time the x-ray is radiated. These multiple x-ray fluoroscopic images are synthesized together by the CT image generator 48 to produce a single CT image Pb, utilizing, for example, a known back projection technique.

The PET image PA and the CT image Pb are input into the image superimposer 23. When a tomographic image is presented on the display 36 as the superimposed image P1 generated by the image superimposer 23, the inspection ends. Alternatively, a tomographic image may also be presented on the display 36 as a synthetic image comprised of a PET image PA and a CT image Pb yet to be superimposed one upon the other.

As can be seen from the foregoing description, a radiation tomography apparatus according to the present disclosure includes a device associated with a CT gantry 45 including a top board 10 as an attachment, and a device associated with a PET gantry 11. The device associated with the PET gantry 11 is attachable and removable to/from the device associated with the CT gantry 45. This radiation tomography apparatus can reduce positional misalignment between images captured by the respective devices. According to the present disclosure, a correction is made in order to position a subject image captured by the device associated with the PET gantry 11 and a subject image captured by the device associated with the CT gantry 45 with respect to each other based on a calibration image captured to shoot, in a single field of view, a marker m attached to the PET gantry 11 and a marker m attached to the CT gantry 45. This configuration allows for positioning the subject images with respect to each other with the misalignment of the CT gantry 45 with respect to the PET gantry 11 taken into account. Consequently, no positional misalignment occurs between the subject image captured by the device associated with the PET gantry 11 and the subject image captured by the device associated with the CT gantry 45.

In the radiation tomography apparatus, one of the device associated with the PET gantry 11 or the device associated with the CT gantry 45 captures an image representing the form of the subject M, and the other captures an image representing the distribution of a pharmaceutical in the subject. This allows for precisely positioning an anatomical image and a functional image with respect to each other.

Moreover, as described above, if the markers m attached to the gantries are retained by holders H, the positional relationship between the markers m retained by the holders H does not change. This thus allows for sensing the positional relationship between the gantries more accurately.

The present disclosure shall not be limited to the configurations but may be modified in the following manner.

(1) In the embodiment described above, the PET device is supposed to be attachable and removable to/from the stationary CT device. However, this is only a non-limiting exemplary embodiment of the present disclosure. Alternatively, the apparatus may also be configured such that a CT device is attachable and removable to/from a stationary PET device. Optionally, another apparatus according to the present disclosure may include a different kind of device, such as a magnetic resonance imaging (MRI) device, instead of the CT device. Still alternatively, a radiotherapy device having a gantry may substitute for the CT device or the PET device according to the present disclosure. That is to say, the apparatus of the present disclosure may be configured such that a radiotherapy device is attachable and removable to/from a stationary CT device, PET device, or MRI device or that a CT device, PET device, and/or MRI device are/is attachable and removable to/from a stationary radiotherapy device.

(2) In the embodiment described above, the PET gantry 11 and the CT gantry 45 are supposed to have the same shape. However, this is only a non-limiting exemplary embodiment of the present disclosure. The gantries 11 and 45 may have different shapes when viewed in the z-direction. In that case, before calculating a correction condition, the correction condition calculator 26 performs conversion processing in advance on the three-dimensional map showing a positional relationship between the line segments La and Lb. That is to say, the correction condition calculator 26 transforms the line segment La, derived from the CT gantry 45 on the three-dimensional map such that the CT gantry 45 observed in the z-direction has the same shape as the PET gantry 11 observed in the z-direction. Such a transformation causes the line segments La and Lb on the three-dimensional map to have a positional relationship to be captured when the gantries of the same shape as illustrated in FIG. 9 are captured. The correction condition calculator 26 calculates a correction condition, which has already been described with reference to FIG. 9 and the drawings that follows it, with respect to the three-dimensional map subjected to such conversion processing.

(3) In the embodiment described above, the image corrector 22 is configured to make correction on the PET image Pa. Instead, the image corrector 22 may be configured to make a correction on the CT image Pb.

(4) The correction condition may be represented by a rotation matrix and a translation vector.

What is claimed is:

1. A radiation tomography apparatus comprising:
    a first gantry which has an opening to receive a subject therethrough;
    a top board on which the subject is placed, the top board being attached to a device associated with the first gantry;
    a top board mover configured to move the top board in a direction in which the opening extends with respect to the first gantry;
    a device associated with a second gantry which is attachable and removable from the device associated with the first gantry, the second gantry having an opening to receive the top board on which the subject is placed;

a corrector configured to make a correction for positioning a subject image captured by the device associated with the first gantry with respect to a subject image captured by the device associated with the second gantry; and wherein the corrector makes the correction for positioning the subject images based on a calibration image captured to shoot, in a single field of view, a marker attached to the first gantry and a marker attached to the second gantry.

2. The apparatus of claim 1, wherein one of the device associated with the first gantry or the device associated with the second gantry captures an image representing a form of the subject, and the other one of the devices captures an image representing a distribution of a pharmaceutical in the subject.

3. The apparatus of claim 1, wherein one of the device associated with the first gantry or the device associated with the second gantry is a radiotherapy device.

4. The apparatus of claim 1, wherein the first gantry is provided with a holder which is configured to retain positions of a plurality of markers that are attached to the first gantry and that include the marker.

5. The apparatus of claim 1, wherein the second gantry is provided with a holder which is configured to retain positions of a plurality of markers that are attached to the second gantry and that include the marker.

6. The apparatus of claim 1, wherein the corrector makes the correction for positioning by performing, in combination, a correction including translation of the subject images and a correction including rotation of the subject images.

7. The apparatus of claim 1, further comprising;

an optical tracker configured to capture the calibration image.

8. The apparatus of claim 1, further comprising a superimposer configured to superimpose the subject images, on which the correction for positioning has been made, one upon the other to generate a superimposed image.

* * * * *